United States Patent [19]

Fischer

[11] Patent Number: 4,986,820
[45] Date of Patent: Jan. 22, 1991

[54] SYRINGE APPARATUS HAVING IMPROVED PLUNGER

[75] Inventor: Dan E. Fischer, Sandy, Utah

[73] Assignee: Ultradent Products, Inc., Salt Lake City, Utah

[21] Appl. No.: 370,618

[22] Filed: Jun. 23, 1989

[51] Int. Cl.⁵ .............................................. A61M 5/315
[52] U.S. Cl. ................................................ 604/218
[58] Field of Search ................ 604/218, 187, 199, 220

[56] References Cited

U.S. PATENT DOCUMENTS

| | | |
|---|---|---|
| 2,575,425 | 11/1951 | Nelson . |
| 2,812,763 | 11/1957 | Feguson . |
| 3,026,872 | 3/1962 | Prater, Jr. . |
| 3,277,894 | 10/1966 | Alexander . |
| 3,656,480 | 4/1972 | Rubricius . |
| 3,738,539 | 6/1973 | Belch .................................... 222/341 |
| 3,766,918 | 10/1973 | Kessel . |
| 4,201,209 | 5/1980 | LeVeen . |
| 4,467,065 | 8/1984 | Williams et al. .................. 604/199 X |
| 4,708,270 | 11/1987 | Ruesch ............................ 222/386.5 |

FOREIGN PATENT DOCUMENTS

| | | | |
|---|---|---|---|
| 238277 | 4/1962 | Australia ............................. 604/218 |
| 2948658 | 6/1981 | Fed. Rep. of Germany ...... 604/220 |
| 1242553 | 8/1960 | France ................................ 604/218 |
| 1333235 | 6/1963 | France ................................ 604/218 |

Primary Examiner—John D. Yasko
Attorney, Agent, or Firm—Workman, Nydegger & Jensen

[57] ABSTRACT

An improved syringe apparatus in which the plunger tip is fabricated as a unitary part of the plunger. The plunger tip is provided with two contact members in contact with the cylindrical bore wall of the syringe barrel. The first contact member is provided by a circular rim which is bowl shaped and which projects forwardly at the end of the plunger. The second contact member is provided by a circular ring located slightly behind the first sealing member. The entire plunger, including both contact members, are preferably fabricated as a unitary structure from, for example, polypropylene or other material which is relatively resistant to degradation due to chemicals stored over prolonged periods of time in the syringe barrel.

13 Claims, 2 Drawing Sheets

FIG. 2A

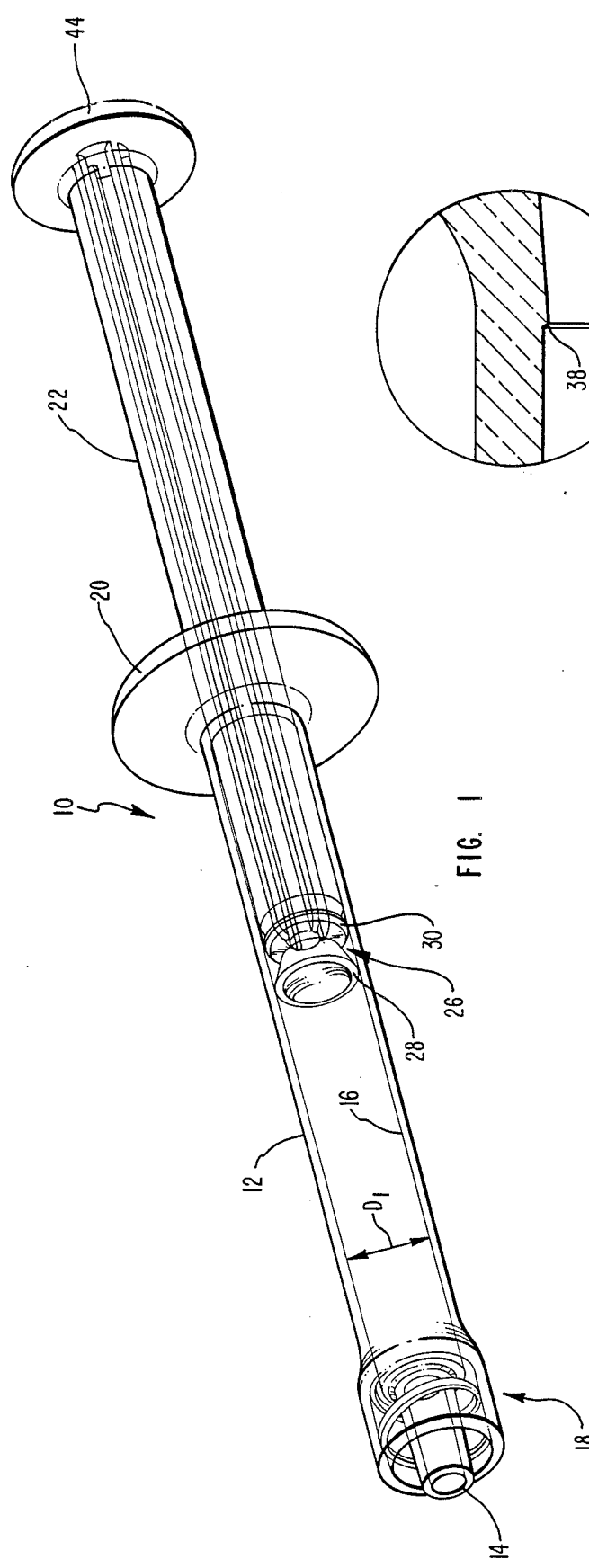
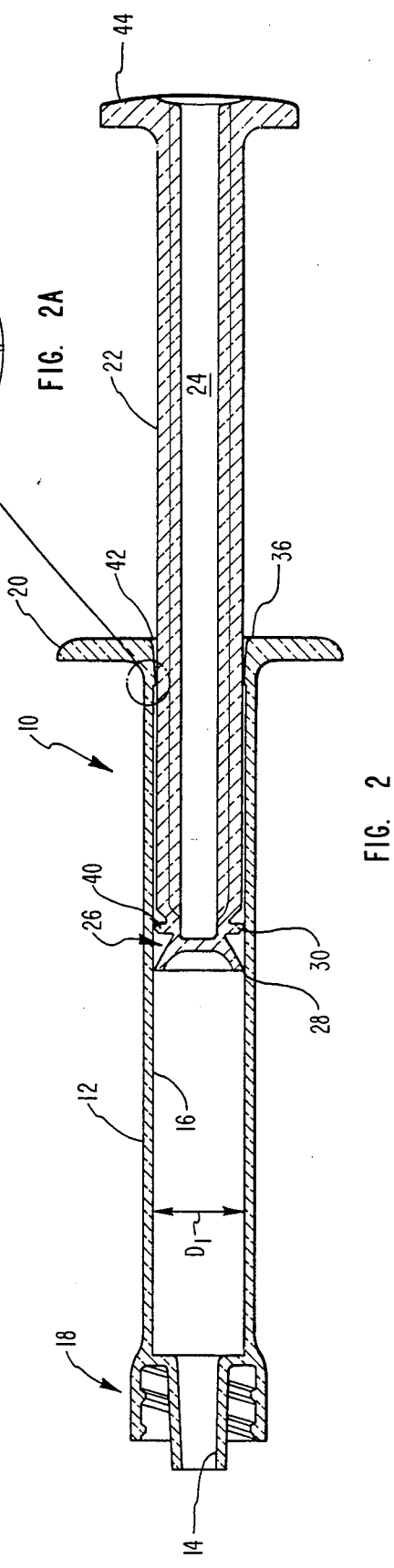

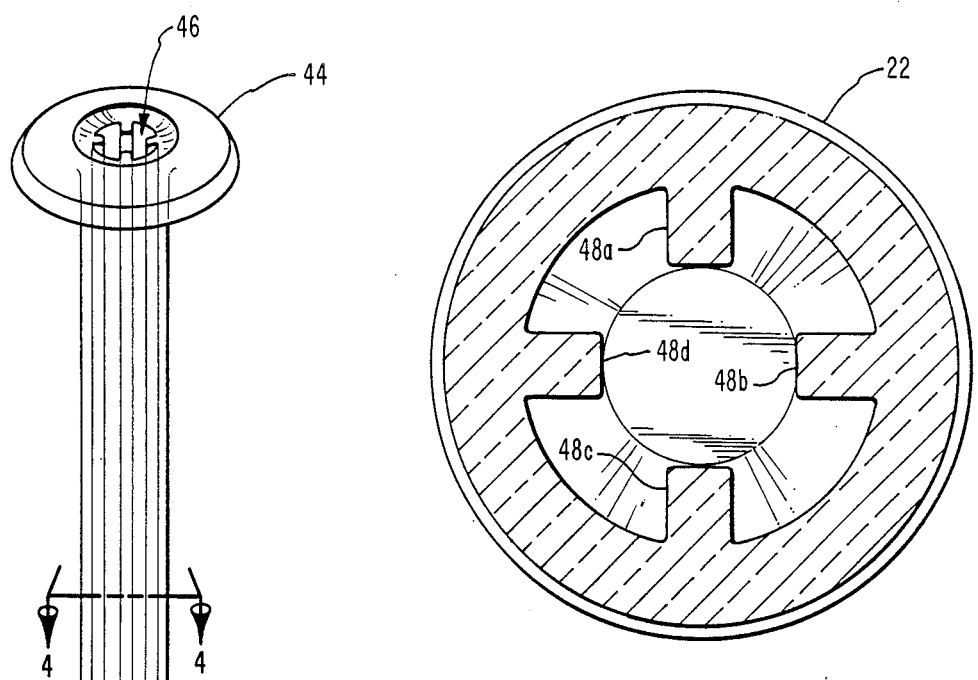
FIG. 3
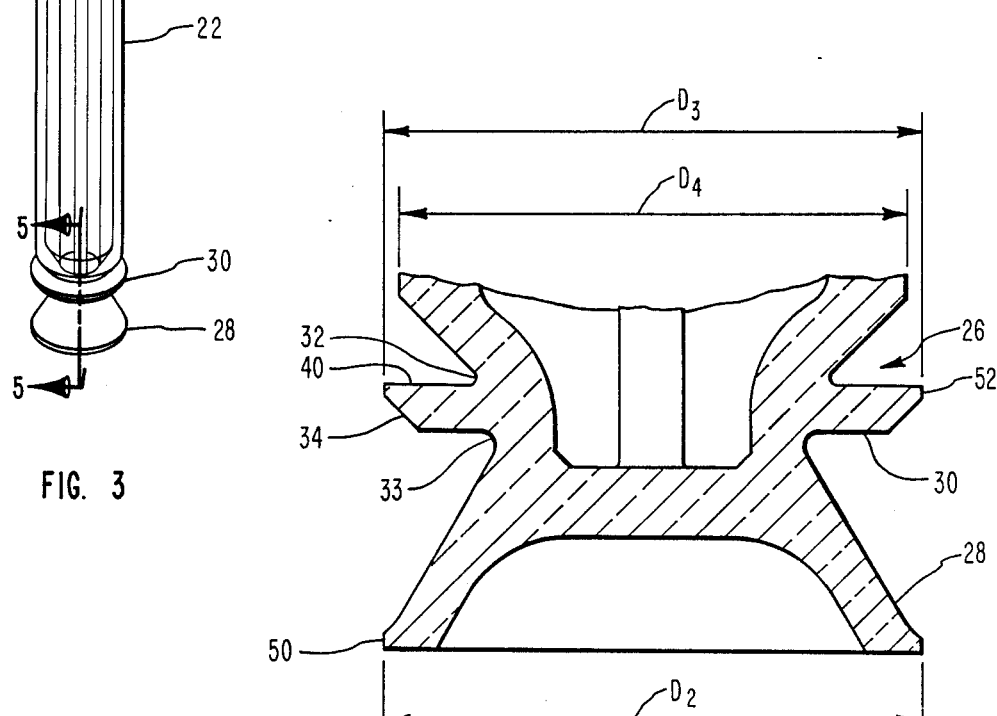
FIG. 4
FIG. 5

SYRINGE APPARATUS HAVING IMPROVED PLUNGER

BACKGROUND

1. Field of the Invention

This invention relates to a syringe apparatus. More particularly, the present invention is directed to a novel syringe plunger for a syringe particularly adapted for preloading with, and storage of, a fluid ready to be dispensed.

2. The Prior Art

Many aspects of modern society have come to rely upon ready-to-use products which are used once and then disposed. In many situations, the use of ready-to-use disposable items achieves considerable cost savings since time and expense is not required to clean and ready the item for reuse.

For example, in the medical and dental professions, the widespread acceptance of ready-to-use disposable items not only results in considerable cost savings, but also increases patient safety by reducing the risk of infection because of inadequate cleaning and sterilization. Moreover, having a supply of ready-to-use disposable items insures that the particular item will be immediately available when needed without waiting for the item to be prepared.

One common example of a ready-to-use disposable item widely accepted in the medical and dental professions is the preloaded disposable syringe. A wide variety of fluids, ranging from drugs stored and ready for hypodermic injection to topical agents used in the dental profession, as well as other fluids, are stored in preloaded syringes which are kept on hand waiting to be used.

As is widely understood by health-care professionals and others, many fluids, whether used in a health care or industrial setting, have a limited shelf life. Once the shelf life of a fluid stored in a preloaded syringe is reached, it is ill advised, or even unsafe, to use the preloaded syringe. Thus, health-care providers must keep only enough supply on hand as will be used prior to reaching the maximum shelf life or incur the expense of discarding unused items.

Unfortunately, in the case of preloaded syringes, there are many instances wherein the syringe itself in which the fluid is stored contributes to a shorter than usual shelf life. In many instances, the shelf life of the fluid may be extended by merely fabricating the syringe from an opaque material thus blocking out energy and the like and near light portions of the spectrum which accelerate deterioration of the fluid and its reaction with the syringe materials. In other cases, storage of fluid in a disposable syringe affects the shelf life of the fluid little, if at all.

Nevertheless, syringes which have commonly been used in the art for such applications contributed to the shortened shelf life of the fluid contained therein. For example, in the dental profession, chemicals such as phosphoric acid and hydrofluoric acid are used to etch dental materials with excellent results. Nevertheless, compositions such as these are harsh chemicals which must be properly handled and used with care. As with other compositions used in the health-care profession, these harsh chemicals are also desirably packaged in preloaded disposable syringes which are kept on hand ready for use.

The prior art type syringes used in such applications generally comprise a syringe body or barrel having a bore formed therein. A plunger is inserted into the bore and thus any fluid contained within the syringe barrel may be expelled by pushing the syringe plunger into the barrel. Since a fluid tight seal is required between the plunger and the wall of the barrel, a resilient rubber-like tip is positioned on the end of the plunger. Unfortunately, materials from which such resilient rubber-like tips are fabricated many times tend to deteriorate in the presence of solutions of phosphoric and hydrofluoric acids, or some of the alcohol or harsh solvents and resins that are used in the dental profession. Deterioration of the plunger tip leads to both contamination of the solution within the syringe as well as decreasing the efficiency of the seal between the plunger and the bore wall.

Other prior art type syringes have replaced the rubber-like tip with a generally flat, circular disk that can be made as part of the plunger so that the disc is more resistant to corrosion. This type of syringe does not, however, glide smoothly in the syringe barrel nor does it provide a seal that is as effective as the rubber-like tip syringe plungers.

Thus, the prior art has not provided a suitable syringe apparatus which combines the advantages of a smooth glide when the syringe plunger moves through the syringe barrel, as obtained with rubber-tipped plungers, with the corrosion-resistant characteristics of non-rubber tipped plungers, which are advantageous for prolonging shelf life of chemicals of a harsher nature that may be packaged and stored in such syringes.

OBJECTS AND BRIEF SUMMARY OF THE INVENTION

In view of the present state of the art, it is a primary object of the present invention to provide an improved syringe apparatus for use in storing chemical agents therein until the syringe is used, without deteriorating the plunger tip and thereby increasing shelf life.

It is another object of the present invention to provide a syringe apparatus wherein all liquid-contacting portions of the apparatus are fabricated from stable materials that are chemically resistant to deterioration.

Another important object of the present invention is to provide a syringe apparatus wherein the plunger tip is fabricated as a unitary part of the plunger structure.

It is yet another object of the present invention to provide a syringe apparatus wherein the plunger tip maintains a smooth, stable glide while still maintaining an effective sealing contact with the syringe barrel as the syringe plunger is pushed through the barrel.

Additional objects and advantages of the invention will be apparent from the description and claims which follow, or may be learned by the practice of the invention.

Briefly summarized, the foregoing objects and advantages are realized in an improved syringe apparatus. In the presently preferred embodiment, the apparatus comprises a syringe barrel. Provided in the syringe barrel is an elongated cylindrical bore having an aperture at one end.

A plunger is provided within the cylindrical bore and the sliding movement of the plunger within the bore causes liquid to be drawn up into or expelled from the syringe. Advantageously, the plunger tip is fabricated as a unitary part of the plunger. The plunger tip is provided with two members in contact with the cylindrical bore wall.

The first member is a sealing member provided by a circular rim projecting forwardly from the plunger so that a conical shape is formed at the end of the plunger. The second member is for maintaining a smooth, stable glide and for providing a secondary seal, and is provided by a circular ring extending substantially perpendicularly from the plunger. In the presently preferred embodiment, the syringe body and plunger, including the first and second members provided on the plunger tip, may be fabricated from polypropylene. Thus, the plunger tip is not fabricated of a resilient material susceptible to deterioration from liquids such as dental agents but yet is somewhat flexible to enable an adequate, fluid-tight seal.

The first and second members ensure that a secure seal is maintained as the plunger slides smoothly and stably within the cylindrical bore. The forward projecting rim provided at the tip of the plunger is formed such that as the plunger is manually forced into the cylindrical bore the rim will tend to slightly expand the interior wall of the barrel, increasing the sealing contact with the cylindrical bore. The perpendicularly extending rim provides a secondary fluid seal and helps to stabilize the plunger.

BRIEF DESCRIPTION OF THE DRAWINGS

A more particular description of the invention will be rendered by reference to the presently preferred embodiment, the best mode thereof which is illustrated in the appended drawings. Understanding that these drawings depict only one embodiment of the invention and are therefore not considered to be limiting of its scope, the presently preferred embodiment and the presently understood best mode of the invention will be described with additional detail through use of the accompanying drawings in which:

FIG. 1 is a perspective view illustrating the presently preferred embodiment of the apparatus of the present invention.

FIG. 2 is a cross-sectional view of the embodiment shown in FIG. 1 taken along its entire length.

FIG. 2A is an enlargement of the cross-sectional view of the area indicated in FIG. 2.

FIG. 3 is a perspective view of the plunger of the described embodiment.

FIG. 4 is a cross-sectional view of the plunger taken along line 4—4 of FIG. 3.

FIG. 5 is a cross-sectional view of the plunger taken along line 5—5 of FIG. 3.

DETAILED DESCRIPTION OF THE PREFERRED EMBODIMENT

The components of the present invention, as generally described and illustrated in the figures herein, may be arranged and adapted to a wide variety of different applications. For example, although the embodiment described therein is particularly adapted for dispensing dental agents which have been preloaded into the syringe, the present invention may be used for other applications, including but not limited to medical, scientific, and industrial applications.

Referring first to FIG. 1, the overall apparatus of the present invention is generally indicated at 10. As hereinafter more fully described, the apparatus is comprised of a barrel means for containing a fluid. The barrel means comprises a barrel 12 having a longitudinal bore therein with a diameter as indicated at D1 in FIG. 2. In the described embodiment, it is preferred that the diameter D1 of the bore be of a uniform diameter along the length of the barrel 12. The barrel means further comprises an aperture 14 through which liquid is expelled from the barrel means.

The apparatus further comprises a plunger means for expelling fluid through the aperture. The plunger means comprises both a first and a second contact means. In the described embodiment, the bore provided in the barrel means is preferably cylindrical and fabricated with a smooth bore wall 16. The first and second contact means are disposed on one end of the plunger means and spaced apart from each other. Both the first and the second contact means are in contact with the bore wall 16 such that both the first and the second contact means provide a slidable fluid seal with the wall 16 as the plunger means is pushed into the barrel means.

The first and the second contact means may preferably be fabricated from the same material and as a unitary structure with the remainder of the plunger means. The first and second contact means are also preferably fabricated from a relatively noncompressible, flexible material such as polypropylene or polyethelene. By providing the plunger structure as hereinafter more fully described, the syringe apparatus of the present invention is ideally suited for preloading with many different formulations of liquid compounds, such as dental agents, since the complete plunger means may be fabricated from the same material as the barrel means, which is more resistant to chemical degradation caused by such agents, while still maintaining an effective fluid seal and a smooth, stable guide.

Positioned at one end of the syringe barrel 12 is a luer lock connector generally designed at 18. Inclusion of a luer lock connector 18 allows fluid directing devices such as tubing, nozzles, or needles to be attached thereto and to direct the fluid as it is expelled from the syringe barrel 12. Also represented in FIGS. 1 and 2 is a finger rest 20. The finger rest 20 is formed to allow the user to place the syringe barrel 12 between, for example, the index and middle finger to provide a secure grip thereon.

Preferably the syringe barrel 12, as well as all other components of the illustrated embodiment, may be fabricated from a material such as polypropylene. Utilizing a material such as polypropylene allows the syringe apparatus represented in the drawings to be preloaded with many different formulations and to resist deterioration caused by the same. Moreover, those skilled in the art will appreciate that the structures of the described embodiment may be economically manufactured utilizing injection molding techniques as well as other manufacturing methods.

Referring to FIGS. 2 and 3, further details concerning the structure of syringe barrel 12 as well as the plunger means will be described. FIG. 2 is a cross-sectional view taken along the length of the syringe barrel 12 and plunger means and FIG. 3 is an enlargement of the tip of the plunger means. As can be seen in FIGS. 2 and 3, the plunger means comprises a plunger body 22 having a hollow core, generally designated 24. Also illustrated is a cross-sectional view of the plunger tip, generally designated at 26. In the described embodiment the plunger tip 26 is formed so as to comprise the aforementioned first contact means by the contact between rim 28 and barrel wall 16. Also, the plunger tip 26 is formed so as to provide the aforementioned second contact means comprising ring 30 which also contacts bore wall 16.

The plunger tip 26 is notched at 32 just behind ring 30. This permits a slight amount of flexibility so that ring 30 can bend slightly to the rear as plunger body 22 is pushed through barrel 12. The leading edge 34 of ring 30 is also angled to facilitate movement of tip 26 as plunger body 22 is pushed forward. Rim 28 has a conical shape, as shown best in FIG. 1, which helps to provide a satisfactory fluid-tight seal with the interior wall 16 of barrel 12.

Also represented in FIG. 2 is a structure functioning as a means for preventing removal of the plunger means from the barrel means. As shown in the enlarged portion of FIG. 2A, the open end 36 of syringe barrel 12 is provided with a narrowed diameter which forms a ridge 38. When plunger body 22 is being withdrawn from the syringe barrel 12, the trailing edge 40 (see also FIG. 5) of ring 30 will contact ridge 38 and prevent complete removal of the plunger from barrel 12. Nevertheless, if desired, by increasing the withdrawal force on the plunger the flexibility of the syringe barrel 12 and ring 30 will allow the plunger to be removed completely from the syringe barrel 12. Furthermore, as shown in FIG. 2, the open end 36 of syringe barrel 12 is provided with a widened, gently sloping opening 42 to allow the plunger to be readily inserted into syringe barrel 12.

The structure of the plunger tip 26, as will be hereinafter more fully explained, provides a secure fluid seal between the plunger tip 26 and the wall 16 of syringe barrel 12 and also provides for stability and a smooth glide as the plunger slides within the syringe barrel 12.

As shown in FIG. 5, the first contact means is comprised, for example, of the forward extending bowl-shaped rim 28, with a first sealing surface 50. It will be noted that the diameter of the cylinder defined by the first sealing surface is indicated at D2 in FIG. 5. The second contact means is comprised of, for example, the circular ring 30 and a second sealing surface 52. The diameter of the second sealing surface is indicated at D3 in FIG. 5 while the diameter of plunger body 22 is represented at D4.

While the plunger tip 26 and preferably the entire plunger body 22 are fabricated as a single unitary structure from a nonresilient material which also possesses a relatively high surface hardness when compared to natural or synthetic rubber materials, the notched areas 32 and 33 combined with the material properties, thickness, and physical dimensions such as length, angular orientation, etc. all combine to allow the rim 28 and ring 30 an appropriate amount of flexibility.

Importantly, the diameter D4 of syringe body 22 is less than the diameter D1 shown in FIG. 1 of the interior bore of syringe barrel 12. Thus, plunger body 22 does not contact the bore wall 16. For example, diameter D1 (FIG. 2) may preferably be 0.252 inches while diameter D4 (FIG. 5) may preferably be 0.240 inches.

The diameters D2 and D3 of sealing surfaces 50 and 52 are preferably slightly greater than the diameter D1 of the barrel bore, with diameter D3 being slightly less than D2 but still larger than D1. For example, in the illustrated embodiment of FIG. 5, D2 may be 0.256 inches and D3 may be 0.254 inches. Plunger rim 28 and ring 30 will flex slightly as the plunger tip 26 is inserted into the barrel bore. By utilizing the described structure, a fluid-tight, slidable seal is provided between the plunger tip 26 and the bore wall 16.

Referring now to FIG. 3, additional detail of the syringe plunger is shown. FIG. 3 is a perspective view showing the length of the plunger. The plunger is provided with a generally flat rest 44 which is adapted for receiving the thumb, finger, or palm of the user as the user applies pressure to the plunger.

As mentioned previously, a preferred material from which to fabricate the plunger is polypropylene. Thus, the transparency of the preferred material is illustrated in FIG. 3 and shows that the plunger is provided with a hollow internal cavity along its length, generally designed 46 in FIG. 3. Providing the plunger with a hollow cavity 46 requires that less material be used to fabricate the plunger, and also reduces cooling time of molding processes.

Referring to FIGS. 3 and 4, since the plunger tip 26 and body 22 are made of a relatively softer plastic, to prevent distortion when cooling and in order to provide increased rigidity and strength to the plunger, a plurality of ribs 48a-48d extend into the hollow cavity 26 from the plunger body 22. The ribs 48a-48d provide additional rigidity and strength to plunger body 22.

As explained previously, the presently preferred embodiment provides the advantages of a plunger tip 26 which is unitary with the plunger body 22 and is thus fabricated from a material which is resistant to deterioration or reaction with chemical formulations which may be preloaded into the syringe and left for relatively long periods of time while still retaining the characteristics of rubber-tipped plungers in terms of stability and smooth glide.

Another advantage is that as the user increases pressure on the syringe plunger, such as when a particularly viscous formulation is contained within the barrel 12, the conical shape of the rum 28 will cause the first contact surface 50 to be pressed against the bore wall 16 with even greater force, ensuring an adequate seal, which is backed up by the second contact surface 52.

The invention may be embodied in other specific forms without departing from its spirit or essential characteristics. The described embodiments are to be considered in all respects only as illustrative and not restrictive. The scope of the invention is, therefore, indicted by the appended claims rather than by the foregoing description. All changes which come within the meaning and range of equivalency of the claims are to be embraced within their scope.

What is claimed is:

1. A syringe comprising:
   barrel means for containing a fluid, said barrel means comprising a bore provided therein and having a bore wall which has a first diameter and aperture means through which said fluid is expelled; and
   plunger means for expelling the fluid from the barrel means through the aperture means, said plunger means having a tip comprising a first contact means for maintaining a fluid-tight seal with said bore wall, said first contact means comprising a diameter slightly greater than said first diameter and said tip further comprising a second contact means for maintaining stability and providing a smooth glide of said plunger means in said bore, and for providing a secondary fluid seal, said second contact means comprising a diameter slightly greater than said first diameter but slightly less than the diameter of said first contact means, and wherein the tip and said first and second contact means are formed from the same material and as a unitary part of said plunger means.

2. A syringe as defined in claim 1 wherein the barrel means comprises a material which is semitransparent.

3. A syringe as defined in claim 1 further comprising means for restricting the removal of the plunger means from the barrel means.

4. A syringe as defined in claim 3 wherein said restricting means comprises a ridge on the bore wall.

5. A syringe as defined in claim 1 wherein the plunger means further comprises:
   a hollow cavity extending for a substantial portion of the length of the plunger means; and
   a plurality of ribs formed on the interior of the hollow cavity and along the length thereof.

6. A syringe as defined in claim 1 wherein the barrel means further comprises a threaded coupling disposed at the aperture, said threaded coupling formed as a unitary structure with the barrel means.

7. A syringe as defined in claim 1 wherein said first contact means comprises a forwardly extending, bowl-shaped rim member having a first sealing surface.

8. A syringe as defined in claim 7 wherein said second contact means comprises a ring member having a second sealing surface, said ring member being positioned behind said rim member and separated therefrom buy a first notched area, and having a second notched area formed behind said ring member.

9. A syringe comprising:
   a syringe barrel having a bore provided therein which has a first diameter and an aperture formed in a first end of the syringe body; and
   a plunger means slidably movable within the bore of the plunger means comprising, as a unitary part thereof formed of the same material, a tip comprising:
      a first contact means for making a fluid-tight slidable contact with the bore wall, said first contact means comprising a forwardly extending bowl-shaped rim member, said rim member having a diameter slightly greater than said first diameter; and
      a second contact means for stabilizing said plunger means and for making a second fluid-tight contact with the bore wall, said second contact means comprising an annular, essentially flat ring member extending in an essentially perpendicular orientation relative to said bore wall, said ring member having a diameter slightly greater than said first diameter but slightly less than the diameter of said rim member, and said ring member being located at essentially the base of said rim member; and
   said plunger means further comprising a plunger body, the first and second contact means and the plunger body comprising a unitary structure all of the same material.

10. A syringe as defined in claim 9 wherein said barrel and plunger means are formed of polypropylene.

11. A syringe as defined in claim 9 further comprising means for restricting the removal of said plunger means from the barrel.

12. A syringe as defined in claim 11 wherein said restricting means comprises a ridge on the bore wall.

13. A syringe plunger for use with and insertion into a syringe barrel to form a syringe, the syringe barrel having a first diameter and the syringe plunger comprising:
   an elongated body having first and second ends, the elongated body having a diameter which is less than the first diameter of the bore provided in the syringe barrel;
   a rest surface provided at the first end of the elongated body, the rest surface being adapted to receive a portion of a user's hand; and
   a plunger tip disposed at the second end of the elongated plunger body, and formed from the same material as a unitary structure therewith, the plunger tip comprising:
      a first contact surface comprised of a non-resilient material projecting from the plunger tip; and
      a second contact surface comprised of a non-resilient material projecting from the plunger tip between the first contact surface and the first end of the elongated body, the first and the second contact surfaces each having a diameter which is slightly greater than the diameter of the bore provided in the syringe barrel so as to each provide a fluid-tight seal therewith, but the diameter of the second contact surface being slightly less than the diameter of the first contact surface.

* * * * *

UNITED STATES PATENT AND TRADEMARK OFFICE
CERTIFICATE OF CORRECTION

PATENT NO. : 4,986,820

DATED : January 22, 1991

INVENTOR(S) : DAN E. FISCHER

It is certified that error appears in the above-identified patent and that said Letters Patent is hereby corrected as shown below:

```
Column 2, line 15, after "as" (second occurrence) insert --to--
Column 3, line 31, delete "which is" and insert therefor --being--
Column 6, line 35, "rum 28" should be --rim 28--
Column 6, line 43, "indicted" should be --indicated--
Column 7, line 26, "buy" should be --by--
```

Signed and Sealed this

Eighth Day of December, 1992

*Attest:*

DOUGLAS B. COMER

*Attesting Officer*     *Acting Commissioner of Patents and Trademarks*